United States Patent [19]
Wang

[11] Patent Number: 6,051,700
[45] Date of Patent: Apr. 18, 2000

[54] PROCESS AND METHOD FOR HYDROXYALKYLATION OF STARCH AND HYDROXYALKYL STARCH PREPARED ACCORDINGLY

[75] Inventor: Jiao Wang, Muscatine, Iowa

[73] Assignee: Grain Processing Corporation, Muscatine, Iowa

[21] Appl. No.: 09/248,452

[22] Filed: Feb. 11, 1999

[51] Int. Cl.$^7$ .............................. C08B 31/10; C12P 19/14
[52] U.S. Cl. ................. 536/111; 435/99; 127/36; 536/114
[58] Field of Search .................... 536/111, 124; 435/99, 201; 127/36

[56] References Cited

U.S. PATENT DOCUMENTS

| | | | |
|---|---|---|---|
| 2,516,632 | 7/1950 | Kesler et al. | 260/233.3 |
| 2,516,634 | 7/1950 | Kesler et al. | 260/209 |
| 2,845,417 | 7/1958 | Kesler et al. | 260/233.3 |
| 4,016,354 | 4/1977 | Greenwood | 536/111 |
| 4,048,434 | 9/1977 | Speakman | 536/105 |
| 4,167,622 | 9/1979 | Holzer | 536/111 |
| 4,281,111 | 7/1981 | Hunt et al. | 536/111 |
| 4,451,649 | 5/1984 | Teubner et al. | 536/111 |
| 4,452,978 | 6/1984 | Eastman | 536/111 |
| 4,474,951 | 10/1984 | Pope | 536/95 |
| 4,629,698 | 12/1986 | Nitsch et al. | 435/95 |
| 5,888,781 | 3/1999 | Sierks et al. | 435/99 |

OTHER PUBLICATIONS

Perera et al., "The Reactivity of Porcine Pancreatic alpha–Amylase Towards Native, Deffated and Heat–moisture Treated Potato Starches Before and After Hydroxypropylation", Starch/Strake, vol. 50, No. 5, pp. 206–213, May 1998.

Hoover et al., "Effects of Hydroxypropylation on Thermal Properties, Starch Digestibility and Freeze–Thaw Stability of Field Pea (Pisum sativum cv Trapper) Starch", Starch/Starke, vol. 40, No. 10, pp. 383–387, Oct. 1988.

"Polysaccharides in Medicinal Applications", edited by Severian Dumitriu, publ. by Marcel Dekker, pp. 188–192, 1996.

Eliasson et al., "Starch: Physicochemical and Functional Aspects" (chapter 10 of Carbohydrates in Food), edited Ann–Charlotte Eliasson, publ. by Marcel Dekker, Inc., pp. 431–441, 471–473 and 484–503, 1996.

Kirk–Othmer, Enamels, Porcelain or Vitreous to Ferrites, Encylopedia of Chemical Technology, vol. 9 (1980), pp. 195–199.

Daniel N. Lapedes, Amylase, McGraw–Hill Encyclopedia of Science & Technology, 6$^{th}$ Ed. (1987), p. 493.

*Primary Examiner*—Howard C. Lee
*Attorney, Agent, or Firm*—Leydig, Voit & Mayer, Ltd.

[57] ABSTRACT

Disclosed are a method and process for preparing a hydroxyalkyl starch. In accordance with the disclosed invention, the starch is treated with an enzyme under conditions to increase the susceptibility of the starch to hydroxyalkylation by a hydroxyalkylating agent. After the starch is so treated, the starch is hydroxyalkylated with a hydroxyalkylating agent. The hydroxyalkylation reaction can proceed to provide a starch having an MS greater than about 0.2, while still remaining in granular form in the aqueous suspension. The method of the invention thus provides a granular starch having a higher MS than is otherwise attainable via a reaction in aqueous media.

22 Claims, No Drawings

PROCESS AND METHOD FOR HYDROXYALKYLATION OF STARCH AND HYDROXYALKYL STARCH PREPARED ACCORDINGLY

TECHNICAL FIELD OF THE INVENTION

The present invention pertains to a method for the hydroxyalkylation of starch. More specifically, the invention pertains in the preferred embodiment to a method for preparing a hydroxyalkyl starch in a hydroxyalkylation reaction that is performed in aqueous suspension to yield a highly substituted hydroxyalkyl starch.

BACKGROUND OF THE INVENTION

Hydroxyalkyl starches comprise a commercially important class of chemicals. Such hydroxyalkyl starches are useful in a variety of commercial and industrial applications and for a variety of purposes, such as for enhancing freeze/thaw and cold storage stability, for lowering the gelatinization temperature of mixtures such as in application for meat products, for increasing the viscosity and clarity of gels and pastes, for reducing gel syneresis, and for many other uses. HydroxyaLkyl starches are particularly suitable as food thickeners, and such starches are often used commercially in such applications.

The prior art has provided a number of methods for preparing hydroxyalkyl starches. Conventionally, hydroxyalkyl starches are prepared by reacting starch with an alkylene oxide, generally in the presence of a suitable catalyst, such as an alkali metal hydroxide catalyst. Commonly, such reactions take place in a aqueous slurry or suspension, from which further modification of the starch can be conveniently accomplished and from which the hydroxyalkyl starch can readily be removed and washed. Such conventional processes are further discussed in Whistler et al., *Starch Chemistry and Technology*, 2d. ed. 1984.

The conventional method of hydroxyalkylating starch in aqueous slurry is limited in some respects. The extent of substitution may be measured by the molar substitution ("MS") of the starch, which expresses the number of substituted monomeric units per anhydroglucose unit. It is commonly understood that, when a starch is hydroxyalkylated conventionally in an aqueous suspension to an MS greater than about 0.1, the integrity of the starch granules will become compromised, and the starch will become gelatinized. Starch gelatinization results from the swelling and degradation of the starch granules in the aqueous slurry. If such swelling occurs to an extent that the starch gelatinizes, such gelatinization will lead to substantial difficulties in further processing the finished hydroxylated starch. In particular, gelatinization of the starch will render it difficult to remove soluble reaction by-products, which otherwise could be removed merely by washing. Thus, in commercial practice, the conventional method is limited to the preparation of hydroxyalkyl starches that have an MS of about 0.1 or less.

Besides the conventional method, other methods for preparing hydroxylated starches are also known in the art. In accordance with such methods, hydroxylated starches that have an MS of greater than about 0.1 can be provided. Typically, such methods involve hydroxyalkylating the starch under low-moisture conditions, with the reaction taking place in the dry state or in a non-aqueous medium, such as in an alcoholic medium. Details concerning such methods can be found in one or more of U.S. Pat. Nos. 2,516,632; 2,516,634; and 2,845,417. However, while such methods are useful in obtaining high MS hydroxyalkyl starches, such methods suffer from a number of drawbacks that limit their practicality in commercial applications. Dry state processes are expensive because of the need to protect against explosive hazards presented by starch dust, and because of the special equipment needed. Similarly, reactions in non-aqueous solvents also entail significant additional process costs. The use of such solvents can also present fire and explosion hazards, especially when a lower aliphatic alcohol is used as the reaction medium.

It is a general object of the present invention to provide a method for preparing a hydroxyalkyl starch. In accordance with the preferred embodiments of the present invention, it is another general object to provide a method for preparing a hydroxyalkyl starch in an aqueous medium to provide a hydroxyalkyl starch having an MS greater than about 0.1, whereby the starch remains in granular form after hydroxyalkylation and does not gelatinize.

THE INVENTION

The present invention is premised upon the surprising discovery that starches may be enzymatically treated to increase the susceptibility of the starch to hydroxyalkylation. In accordance with the invention, a method for preparing a hydroxyalkyl starch is provided. The method generally comprises the steps of providing a granular starch, treating the starch with an enzyme under conditions effective to increase the susceptibility of the starch to hydroxyalkylation, and hydroxyalkylating the enzymatically treated starch with a hydroxyalkylating agent to thereby obtain the hydroxyalkyl starch. The starch is preferably provided in an aqueous suspension, and both the enzymatic treatment and hydroxyalkylation reaction are performed while the starch remains in the aqueous suspension. When a starch has been enzymatically treated prior to hydroxyalkylation, the hydroxyalkylation reaction may be allowed to proceed to provide a hydroxyalkyl starch having an MS of greater than about 0.1, while the structural integrity of the starch granule remains intact. Most preferably, the starch remains granular throughout the hydroxypropylation reaction. Because the starch remains in granular form, by-products and other impurities in the aqueous medium may be readily removed by washing, and the granular starch also readily may be modified via further processing steps.

The invention further encompasses a process for preparing hydroxyalkyl starch as set forth hereinabove, the process including the further step of removing the hydroxyalkyl starch from the aqueous suspension. Also encompassed by the present invention is a hydroxyalkyl starch prepared in accordance with the disclosed method and process.

DESCRIPTION OF THE INVENTION

The invention is contemplated to be useful in the preparation of hydroxyalkyl starches from a wide variety of starch sources. Suitable starches include dent corn starch, potato starch, wheat starch, white rice starch, grain sorghum starch, waxy sorghum starch, waxy maize starch, tapioca starch, high amylose maize starch, and other starches. The starch starting material can be modified prior to hydroxyalkylation, or can be an unmodified starch. If modified prior to hydroxyalkylation, the starch can be modified in any suitable manner, such as by acid-thinning or otherwise. Preferably, the starch is provided in the form of an aqueous suspension of starch, in which the water:starch ratio ranges from about 3:1 to about 3:25, preferably about 3:1.5 to about 3:2.

In accordance with the invention, the starch is treated with an enzyme to thereby render the starch more susceptible to hydroxyalkylation with a hydroxyalkylating agent. Any suitable enzyme may be used in accordance with the present invention, and the enzyme thus may be selected from among α-amylase enzymes, β-amylase enzymes, glucoamylase enzymes, amylo-1,6-α-glucosidase enzymes, oligo1,6-α-glucosidase enzymes, isomaltase enzymes, maltotriase enzymes, maltase enzymes, glucosidase enzymes, and starch debranching enzymes. Specific examples of suitable presently commercially available enzymes include CANALPHA 600,000L (bacterial α-amylase available from Biocon, Inc. (U.S.), Lexington, Ky.), BAN 240L (bacterial α-amylase available from Novo Nordisk, Franklington, N.C.) FUN-GAMYL (fungal α-amylase, available from Novo Nordisk), GLUCOAMYLASE AMG 200L (fungal amyloglucosidase, available from Novo Nordisk), PROMOZYME 200L (heat-stable debranching enzyme, available from Novo Nordisk), and so forth. The foregoing list is by no means exhaustive, and it is contemplated that other enzymes may be considered or found to be suitable for use in connection with the present invention.

The action of the enzyme on the starch molecule in rendering the starch more susceptible to hydroxyalkylation is not presently fully understood. While it is not intended to limit the invention to a particular theory of operation, it is believed that various factors may contribute to the increase in susceptibility to hydroxyalkylation of the starch molecule. It is further believed that these factors may vary from enzyme to enzyme and perhaps from starch to starch. For example, it is believed that some enzymes may degrade one or more glucosyl linkages in the starch molecule. Other enzymes may cleave branch points in the starch molecular structure. However, regardless of the exact mechanism of operation, the invention is known to be operative regardless of the correctness of any particular theory as to the mechanism of operation.

The starch should be treated with the enzyme in an amount and manner effective to increase the susceptibility of the starch to hydroxyalkylation. In this respect, the amount of enzyme necessary to achieve the increased susceptibility is expected to vary from enzyme to enzyme. Preferably, at least about 0.10 IU (International Units) enzyme per gram of starch is employed, more preferably from about 0.20 to about 3.30 IU enzyme per gram of starch is employed, and even more preferably, about 0.40 to about 1.60 IU enzyme per gram of starch is employed. To treat the starch, the enzyme is preferably added to the starch suspension and held at a temperature ranging from about 30° to about 60°, most preferably about 40° to 45° C. The pH of the suspension preferably is adjusted to the pH of maximum enzyme activity for the particular enzyme employed; for example, in the case of CANALPHA 600,000 L, the pH of the suspension preferably is adjusted to be between 5.0 and 6.0. Preferably, the enzyme is added to the aqueous starch suspension after the temperature and pH of the suspension have been so adjusted. The enzyme is contacted with and allowed to treat the starch for a period of time sufficient to increase the susceptibility of the starch to hydroxyalkylation, typically a period of from about one hour to about three hours, and preferably about two hours.

At the end of the treatment period, the enzymatic treatment is terminated by adjusting the pH of the suspension, by lowering the temperature, or by otherwise terminating the treatment as may be suitable. At this point, a gelatinization inhibitor may be added to the starch suspension in an amount effective to inhibit the tendency of the starch to become gelatinized in the suspension. Suitable gelatinization inhibitors include sodium chloride and sodium sulfate, and the preferred gelatinization inhibitor is sodium sulfate. The gelatinization inhibitor is preferably added in an amount ranging from about 10 to about 20% by dry basis weight of the starch, more preferably about 15% by dry basis weight.

After the starch has been enzymatically treated and the gelatinization inhibitor optionally added, the starch is hydroxyalkylated by reacting the enzymatically treated starch with a hydroxyalkylating agent. The hydroxyalkylating agent chosen in conjunction with the present invention can be conventional, and suitable hydroxyalkylating agents are disclosed in U.S. Pat. Nos. 2,516,632 and 2,516,634. Generally, hydroxyalkylating agents suitable for use in conjunction with the invention include alkylene oxides containing 2 to about 4 carbon atoms. Examples of suitable species include ethylene oxide, propylene oxide, butylene oxide, and so forth. One preferred hydoxyalkylating agent is propylene oxide.

The hydroxyalkylation reaction may be otherwise conventional, and, in accordance with the preferred embodiments of the invention, the reaction is performed in aqueous suspension. Preferably, the hydroxyalkylating agent is added to the aqueous starch suspension at a pH ranging from about 10.0 to about 13.0, preferably 11.0 to 12.0, in the presence of an alkali metal hydroxide catalyst. Starch is preferably reacted with an amount ranging from about 8% to about 18% by weight of the starch with the hydroxyalkylating agent. The reaction should proceed for a time sufficient to form a starch-hydroxyalkyl ether, and more preferably the reaction should proceed for a sufficient time to provide a starch that has an MS greater than about 0.1. Typically, to achieve such high MS starches, the reaction should be allowed to proceed for at least about 14 hours, more typically about 14 to about 20 hours, and even more typically about 16 to about 18 hours. The reaction may proceed at any suitable temperature, such as a temperature ranging from about 30° to about 50° C., more preferably 40° C. to 45° C. At the conclusion of the hydroxyalkylation reaction, the hydroxyalkylation reaction is terminated, such as by lowering the pH to about 5.5 or below, to yield a hydroxyalkyl starch. While the aforementioned hydroxyalkyating agents and reaction conditions are typical, other hydroxyalkylating agents and reaction conditions as are conventional or as may be found to be suitable also may be employed in conjunction with the present invention.

The method in the invention allows for the preparation of a hydroxyalkyl starch that has an MS greater than about 0.1, and indeed, the hydroxyalkylation reaction may be allowed to proceed to yield a hydroxyalkyl starch having considerably higher molar substitution. Preferably, however, the reaction is terminated while the starch is still granular. The method allows for the preparation of granular starches that have an MS greater than about 0.2. Preferably, a starch having an MS ranging from about 0.14 to about 0.24, and more preferably ranging from about 0.16 to about 0.19, is provided. It is contemplated that granular starches that have even higher degrees of substitution may be realized in conjunction with the invention.

The hydroxyalkyl starch thus prepared is then preferably removed from the aqueous suspension, such as by filtration or other separation of the aqueous medium from the starch. By "removing" is contemplated that granular starch is separated from substantially all of the liquid of the aqueous medium, although of course the starch granules may remain wet and may require further drying for use in some applications. The starch may be further treated or modified prior to or after removing the starch from the aqueous suspension, for example, by cross-linking, bleaching, acid thinning, further substitution, washing, or otherwise treating or modifying the starch. The study may be gelatinizable after hydroxyalkylation.

The following examples illustrate the present invention, but should not be construed as limiting the scope of the present invention.

EXAMPLE 1

Hydroxyalkylation of Starch

Five hundred grams of dry dent corn starch were slurried in water to provide a suspension of 40% solids. The flask containing this suspension was equipped with a vertical shaft and impeller to keep the starch particles in suspension and away from the bottom of the container. The temperature of the suspension was heated to 42° C., and the pH was adjusted to a pH between 5.5 and 6.0.

To the suspension was added 0.131 ml of CANALPHA 600,000L α-amylase, corresponding to 0.82 IU enzyme per gram of starch. The enzyme was allowed to remain in contact with and treat the starch for two hours. At the conclusion of the two-hour period, and with the suspension still held at 42° C., 75 g sodium sulfate, and 143 ml of a sodium hydroxide/sodium chloride solution (5.7 wt. % NaOH, 21.1 wt. % NaCl in water) was added to bring the pH to 11.3. Propylene oxide was added in various amounts, as shown hereinbelow in Table 1 for Examples 1A–1G.

The hydroxypropylation reaction was allowed to proceed for 16 hours. At the conclusion of this period, the pH was reduced to 4.0, and the hydroxypropylated starch was separated from the aqueous medium of the suspension by filtration. The filtered starch was washed with water and dried in a forced air oven at 40° C., then analyzed to determine the degree of substitution. The following results were obtained:

TABLE I

| Example | % Propylene Oxide added (on starch dry basis) | MS |
| --- | --- | --- |
| 1A | 8 | 0.1189 |
| 1B | 10 | 0.1531 |
| 1C | 12 | 0.1673 |
| 1D | 14 | 0.1985 |
| 1E | 16 | 0.2314 |
| 1F | 18 | 0.2480 |
| 1G | 20 | 0.3634 |

Hydroxyalkyl starch having a high MS was obtained in each experiment. When 20% propylene oxide was added, the highest molar substitution was obtained; however, the product was swollen and partially gelatinized after the reaction.

EXAMPLE 2

Hydroxyalkylation of Starch

In this example, propylene oxide was added at 14% on starch dry basis weight. The enzyme CANALPHA 600,000L was added in various amounts prior to the hydroxypropylation reaction to evaluate the quantitative effect of the enzyme addition on the increase in susceptibility to hydroxylation. The following results were observed:

TABLE II

| Example | CANALPHA IU/g | MS |
| --- | --- | --- |
| 2A | 0.28 | .1951 |
| 2B | 0.41 | .1908 |
| 2C | 0.82 | .1985 |
| 2D | 1.64 | .1986 |
| 2E | 3.28 | .1846 |
| 2F | 6.56 | .1665 |

The foregoing results demonstrate that the quantity of enzyme addition has some impact on the resulting degree of substitution of the hydroxypropylated starch.

EXAMPLE 3

Hydroxylation of Various Starches

Various starches were pre-treated with $2.6 \times 10^{-4}$ ml per gram dry starch CANALPHA 600,000L enzyme (0.82 IU/g) in accordance with the teachings of Example 1. The treated starches were then hydroxyalkylated with propylene oxide. The following results were obtained.

TABLE III

| Example | Starch | % PO Added | MS |
| --- | --- | --- | --- |
| 3A | dent | 14 | 0.1985 |
| 3B | waxy corn | 14 | 0.2069 |
| 3C | wheat | 14 | 0.1882 |
| 3D | potato | 14 | * |
| 3E | potato | 10 | 0.1634 |
| 3F | tapioca | 14 | 0.1717 |

*Swollen, not evaluated.

As shown above, starch could be substituted to an MS substantially greater than 0.1 in connection with the present invention. With respect to potato starch, 14% propylene oxide caused gelatinization of the starch, but 10% propylene oxide addition yielded a granular starch. It is believed that the reaction efficiencies correlate to the size of the starch granules for the starches, with the larger granule starches exhibiting greater reaction efficiency. Phosphate ester groups on native potato starch may also affect the reaction efficiency.

EXAMPLE 4

Hydroxyalkylation of Starch/Various Enzymes

The teachings of Example 1 were generally followed to prepare hydroxypropyl dent corn starch using various enzymes. The enzyme was added in each case in the amount of 0.82 IU/g to treat the starch, and the pH of the aqueous suspension was adjusted to the manufacture-recommended activity pH for each enzyme. The following results were observed:

TABLE IV

| Example | Enzyme | MS |
| --- | --- | --- |
| 4A | CANALPHA 600,000L | 0.1985 |
| 4B | FUNGAMYL 800L | 0.2256 |
| 4C | BAN 240L | 0.2317 |

TABLE IV-continued

| Example | Enzyme | MS |
| --- | --- | --- |
| 4D | AMG 200L | 0.2494 |
| 4E | PROMOZYME 200L | 0.2378 |

The foregoing results demonstrate that a hydroxyalkylated starch with a high MS could be achieved in connection with the present invention. The starch that was treated with GLUCOAMYLASE AMG 200L prior to hydroxypropylation had the highest reaction efficiency, and the hydroxyalkylated product was very white. The starch that was pre-treated with CANALPHA 600,000L exhibited a lower reaction efficiency, and the final hydroxyalkylated produced was slightly tan.

EXAMPLE 5

Hydroxyalkylation of Starch with Subsequent Modification

The teachings of Example 1 are followed to prepare a hydroxyalkylated starch. After the starch has been hydroxypropylated, but prior to separation of the starch from the aqueous medium of the suspension, this starch is crosslinked.

The foregoing examples illustrate the preparation of a hydroxyalkyl starch in an aqueous medium. While this is the preferred embodiment of the present invention, the invention is not limited thereto, and indeed the enzyme may be used to treat a starch in connection with the present invention prior to hydroxyalkylation by any other reaction or in any other reaction medium. Similarly, while the hydroxypropylation reaction that is performed in the connection with the present invention preferably provides a granular starch, the invention is not limited thereto, and the hydroxyalkylation reaction may proceed to provide either granular or gelatinized starches. However, in connection at least with the preferred embodiment of the invention, it is seen that the foregoing general objects have been satisfied. The invention provides a method for preparing a granular starch in an aqueous suspension, the starch having an MS greater than about 0.1. The granular, hydroxyalkylated starch prepared in connection with the invention readily can be washed or further modified in the aqueous suspension.

While particular embodiments of the invention have been shown, it will be understood that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and scope of the invention. All references cited herein are hereby incorporated by reference in their entireties.

What is claimed is:

1. A method for preparing a hydroxyalkyl starch, the method comprising the steps of:
   providing a granular starch in an aqueous suspension;
   treating said granular starch with an enzyme under conditions effective to increase the susceptibility of said starch to hydroxyalkylation to thereby obtain a treated starch; and
   hydroxyalkylating said treated starch with a hydroxyalkylating agent; said starch remaining granular in said aqueous suspension during said enzymatic treatment and said hydroxyalkylation.

2. A method according to claim 1, wherein said starch has an MS ranging from about 0.14 to about 0.24 after hydroxyalkylation.

3. A method according to claim 1, wherein said starch is selected from the group consisting of dent corn starch; potato starch; wheat starch; rice starch; grain sorghum starch; waxy sorghum starch; waxy maize starch; tapioca starch; and high amylose maize starch.

4. A method according to claim 1, wherein said enzyme is an enzyme selected from the group consisting of α-amylase enzymes, β-amylase enzymes, glucoamylase enzymes, amylo-1,6-α-glucosidase enzymes, oligo-1,6-α-glucosidase enzymes, isomaltase enzymes, maltotriase enzymes, maltase enzymes, α-glucosidase enzymes and debranching enzymes.

5. A method according to claim 1, wherein said step of enzymatic treatment comprises contacting said starch with an amount ranging from about 0.20 to about 3.30 IU of said enzyme per gram of starch.

6. A method according to claim 1, wherein said step of enzymatic treatment comprises contacting said starch with said enzyme at a temperature ranging from about 40° C. to about 45° C.

7. A method according to claim 1, wherein said hydroxyalkylating agent is an alkylene oxide.

8. A method according to claim 7, wherein said alkylene oxide is selected from the group consisting of ethylene oxide, propylene oxide and butylene oxide.

9. A method according to claim 1, wherein said hydroxyalkylation step comprises reacting said starch with an amount ranging from about 8% to about 18% by weight of said starch of said hydroxyalkylating agent.

10. A method according to claim 1, wherein said starch is treated with said enzyme for about one hour to about three hours prior to hydroxyalkylation.

11. A method according to claim 1, further comprising the step of adding a gelatinization inhibitor to said treated starch prior to hydroxyalkylation.

12. A method according to claim 11, wherein said gelatinization inhibitor is sodium sulfate.

13. A method according to claim 1, wherein said hydroxyalkylation occurs over a period ranging from about 16 hours to about 18 hours.

14. A method according to claim 1, wherein said starch is hydroxyalkylated in the presence of an alkali metal hydroxide catalyst.

15. A suspension of a granular, hydroxyalkyl starch prepared by a process comprising the steps of:
   providing a granular starch in an aqueous suspension;
   treating such granular starch with an enzyme under conditions effective to increase the susceptibility of said starch to hydroxyalkylation to thereby obtain a treated starch; and
   hydroxyalkylating said treated starch to thereby obtain a hydroxyalkyl starch suspension; wherein said hydroxyalkyl starch remains granular in said aqueous suspension during said enzymatic treatment and said hydroxyalkylation.

16. A hydroxyalkyl starch according to claim 15, wherein said hydroxyalkyl starch has an MS ranging from about 0.14 to about 0.24.

17. A hydroxyalkyl starch according to claim 15, wherein said starch is a hydroxyalkyl starch selected from the group consisting of dent corn starch; potato starch; wheat starch; rice starch; grain sorghum starch;

waxy sorghum starch; waxy maize starch; and tapioca starch.

18. A hydroxyalkyl starch according to claim 15, wherein said starch is a hydroxyalkyl starch selected from the group consisting of ethoxylated starch, propoxylated starch, and butoxylated starch.

19. A process for preparing a hydroxyalkyl starch, comprising the steps of:

providing a granular starch in an aqueous suspension;

treating said granular starch with an enzyme in said aqueous suspension under conditions effective to increase the susceptibility of said starch to hydroxyalkylation to thereby obtain a treated starch;

hydroxyalkylating said starch in said aqueous suspension with a hydroxyalkylating agent to thereby obtain a granular, hydroxyalkyl starch; and removing said granular hydroxyalkyl starch from said aqueous suspension.

20. A process according to claim 19, the process comprising the step of further modifying said starch prior to removing said starch from said aqueous suspension.

21. A process according to claim 20, wherein said step of removing said starch from said suspension comprises filtering said aqueous suspension.

22. A process according to claim 19, the process further comprising the step of washing said starch after removing said starch from said aqueous suspension.

* * * * *